(12) United States Patent
Dubois et al.

(10) Patent No.: US 7,910,771 B2
(45) Date of Patent: Mar. 22, 2011

(54) METHOD FOR PRODUCING ACRYLIC ACID FROM GLYCEROL

(75) Inventors: Jean-Luc Dubois, Millery (FR); Christophe Duquenne, Zwickau (DE); Wolfgang Holderich, Frankenthal (DE)

(73) Assignee: Arkema France, Colombes (FR)

( * ) Notice: Subject to any disclaimer, the term of this patent is extended or adjusted under 35 U.S.C. 154(b) by 327 days.

(21) Appl. No.: 11/912,353

(22) PCT Filed: Apr. 24, 2006

(86) PCT No.: PCT/FR2006/000907
§ 371 (c)(1), (2), (4) Date: Oct. 23, 2007

(87) PCT Pub. No.: WO2006/114506
PCT Pub. Date: Nov. 2, 2006

(65) Prior Publication Data
US 2008/0183013 A1    Jul. 31, 2008

Related U.S. Application Data

(60) Provisional application No. 60/689,423, filed on Jun. 10, 2005.

(30) Foreign Application Priority Data

Apr. 25, 2005  (FR) ..................................... 05 04111
Jan. 10, 2006  (FR) ..................................... 06 00183

(51) Int. Cl.
*C07C 51/16*  (2006.01)
(52) U.S. Cl. ........................................ 562/532; 562/545
(58) Field of Classification Search ................. 562/545, 562/532
See application file for complete search history.

(56) References Cited

U.S. PATENT DOCUMENTS

| | | | |
|---|---|---|---|
| 2,558,520 A | 6/1951 | Hoyt et al. | 568/486 |
| 5,387,720 A | 2/1995 | Neher et al. | 568/486 |
| 6,080,898 A | 6/2000 | Drent et al. | 568/861 |
| 6,310,240 B1 | 10/2001 | Contractor et al. | 562/535 |
| 6,403,829 B1 * | 6/2002 | Unverricht et al. | 562/532 |
| 2005/0020851 A1 * | 1/2005 | Olbert et al. | 562/545 |
| 2007/0129570 A1 | 6/2007 | Shima et al. | 562/538 |

FOREIGN PATENT DOCUMENTS

| | | |
|---|---|---|
| EP | 1147807 | 4/2000 |
| EP | 995491 | 10/2001 |
| FR | 695931 | 5/1930 |

* cited by examiner

*Primary Examiner* — Taylor Victor Oh
(74) *Attorney, Agent, or Firm* — Steven D. Boyd

(57) ABSTRACT

The invention relates to a method for producing acrylic acid in one step by an oxydehydration reaction of glycerol in the presence of molecular oxygen. The reaction preferably carried out in gaseous phase in the presence of a suitable catalyst.

11 Claims, No Drawings

METHOD FOR PRODUCING ACRYLIC ACID FROM GLYCEROL

FIELD OF THE INVENTION

The present invention concerns a novel route for the synthesis of acrylic acid, and more particularly relates to the preparation of acrylic acid from glycerol in the presence of molecular oxygen.

BACKGROUND OF THE INVENTION

The main process for the conventional synthesis of acrylic acid uses a catalytic reaction of propylene with a mixture containing oxygen. This reaction is generally performed in the vapor phase, and usually in two steps:
the first step effects the substantially quantitative oxidation of propylene to an acrolein-rich mixture, in which acrylic acid is in minor amount,
the second step effects the selective oxidation of acrolein to acrylic acid.

The reaction conditions for these two steps, performed in two reactors in series, are different and require catalysts that are suitable for the reaction. It is not necessary to isolate the acrolein during this two-step process. The reaction may also be performed in a single reactor, but, in this case, it is necessary to separate out and recycle large amounts of acrolein at the oxidation step.

It has been known for a long time that acrolein may be obtained from glycerol. Glycerol (also known as glycerine) is obtained from the methanolysis of plant oils at the same time as methyl esters, which are themselves used especially as fuels or combustibles in diesel and domestic fuel oil. It is a natural product that has an "environmentally friendly" image, is available in large quantity and may be stored and transported without difficulty. Numerous studies have been devoted to the financial upgrading of glycerol according to its degree of purity, and the dehydration of glycerol to acrolein is one of the routes envisioned.

The reaction involved for obtaining acrolein from glycerol is:

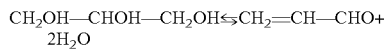

As a general rule, the hydration reaction is favored at low temperatures, and the dehydration reaction is favored at high temperatures. To obtain acrolein, it is thus necessary to use a sufficient temperature, and/or partial vacuum to shift the reaction. The reaction may be performed in the liquid phase or in the gas phase. This type of reaction is known to be catalyzed by acids. Various processes for synthesizing acrolein from glycerol are described in the literature: FR 695 931; U.S. Pat. No. 2,558,520; WO 99/05085; U.S. Pat. No. 5,387,720.

The reaction for the dehydration of glycerol to acrolein is generally accompanied by side reactions leading to the formation of by-products such as hydroxypropanone, propanaldehyde, acetaldehyde, acetone, adducts of acrolein with glycerol, glycerol polycondensation products, cyclic glycerol ethers.

In international patent application WO 2005/073160, the reaction product resulting from the gas-phase dehydration reaction of glycerol is subjected to a subsequent gas-phase oxidation step to obtain acrylic acid. This two-step process is performed with pure glycerol or concentrated aqueous solutions comprising more than 50% by weight of glycerol. Acrylic acid yields of between 55% and 65% are obtained using an alumina-based catalyst impregnated with phosphoric acid and silica for the first dehydration step, and an alumina-supported Mo—V—W—Cu—O mixed oxide for the second oxidation step. The process is performed in two reactors in series, the oxygen being able to be added easily to the gaseous mixture feeding the second reactor. The process may also be performed in a single reactor containing either the two stacked catalysts defining two reaction zones, or the two catalysts as a mixture, this configuration having the drawback of more rapidly deactivating one of the two catalysts, which makes maintenance of the process difficult.

DETAILED DESCRIPTION OF THE INVENTION

Applicants have discovered, surprisingly, that it is possible to obtain acrylic acid directly from glycerol, when the glycerol dehydration reaction is performed in the presence of oxygen. The presence of oxygen makes it possible to perform, in addition to the dehydration reaction, an oxidation reaction, offering the possibility of forming acrylic acid from glycerol in a single step. Supplying oxygen to the reaction medium also has a beneficial effect on reducing the formation of coke on the catalyst used and inhibiting its deactivation, and limiting the formation of by-products such as propanaldehyde, acetone and hydroxypropanone.

A process for producing acrylic acid directly from glycerol is particularly advantageous since it makes it possible to perform the synthesis in a single reactor and thus to reduce the necessary investments.

The principle of the process according to the invention is based on the two consecutive dehydration and oxidation reactions:

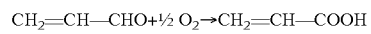

In this reaction scheme, known as oxydehydration, the exothermicity of the oxidation reaction is combined with the endothermicity of the dehydration reaction, which contributes towards better thermal equilibrium of the process.

Another advantage of this process lies in the fact that it is not dependent on a raw material of fossil origin, for instance propylene, but uses a renewable raw material; such a process thus satisfies the criteria associated with the new concept of "green chemistry" within a more global framework of durable development.

One subject of the present invention is thus a process for manufacturing acrylic acid in a single step by oxydehydration reaction of glycerol in the presence of molecular oxygen.

The molecular oxygen may be present in the form of air or in the form of a mixture of gases containing molecular oxygen. The amount of oxygen is chosen so as to be outside the flammability range at any point in the plant. The oxygen content in the process according to the invention will generally be chosen so as not to exceed 20% relative to the mixture of gases entering the reaction (mixture of glycerol/H$_2$O/oxygen/inert gases).

The dehydration reaction of glycerol to acrolein is generally performed on acidic solid catalysts. These catalysts may be chosen from natural or synthetic siliceous materials or acidic zeolites; mineral supports, such as oxides, coated with mono-, di-, tri- or polyacidic inorganic acids; oxides or mixed oxides, or alternatively heteropolyacids. The preferred catalysts are sulfate zirconias, phosphate zirconias, tungsten zirconias, siliceous zirconias, sulfate titanium or tin oxides, and phosphate aluminas or silicas. These acidic catalysts, which are suited to the glycerol dehydration reaction, facilitate the desorption of the acrylic acid produced, but are not optimized for oxidation reactions; the yield of acrylic acid is thus limited with this type of catalyst.

It is therefore preferable, in order to obtain good selectivity towards acrylic acid, for the solid used to be also capable of catalyzing the oxidation reaction. Solids containing at least one element chosen from the list Mo, V, W, Re, Cr, Mn, Fe, Co, Ni, Cu, Zn, Sn, Te, Sb, Bi, Pt, Pd, Ru and Rh, present in metallic form or in the form of oxide, sulfate or phosphate, will preferably be chosen as oxidation catalyst. It is possible to envisage the use of a single catalyst capable of catalyzing both the dehydration reaction and the oxidation reaction, but also to have available a mixture of catalysts, each being capable of effecting one of the two reactions in an optimum manner. This mixture of catalysts is then either an intimate mixture of catalysts, or is in the form of two layers of catalysts stacked in the reactor, the first layer then being capable of effecting the dehydration of glycerol to acrolein, and the second being more suited to the oxidation of the acrolein thus produced into acrylic acid. One or other of these configurations will be adapted as a function of the reactor technology used.

The reaction according to the invention may be performed in the gas phase or in the liquid phase, preferably in the gas phase. When the reaction is performed in the gas phase, various process technologies may be used, i.e. a fixed-bed process, a fluidized-bed process or a circulating fluidized-bed process. In the first two processes, in a fixed bed or a fluidized bed, the regeneration of the catalyst may be separate from the reaction. It may take place ex situ, for example by extraction of the catalyst and combustion in air or with a gaseous mixture containing molecular oxygen. In this case, the temperature and pressure at which the regeneration is performed do not need to be the same as those at which the reaction is performed. According to the process of the invention, it may take place continuously in situ, at the same time as the reaction, given the presence of molecular oxygen or of a gas containing molecular oxygen in the reactor. In this case, the regeneration is likened to an inhibition of deactivation and takes place at the reaction temperature and pressure.

In the circulating fluidized-bed process, the catalyst circulates in two containers, a reactor and a regenerator. Since the glycerol solution vaporization and the dehydration reaction are endothermic, and the oxidation reaction and also the regeneration of the catalyst consisting of the combustion of coke are exothermic, the two systems compensate each other, which contributes towards good thermal equilibrium of the process.

The selection of the optimum process is made as a function of various criteria. The fixed-bed process has the advantage of simplicity. The fluidized-bed processes make it possible to continuously discharge the spent catalyst and to permanently recharge fresh catalyst without stopping the production, with the possibility of being isothermic. The circulating fluidized-bed process has the advantage of optimizing the reaction selectivity by permanently returning freshly regenerated catalyst into the reactor, while at the same time compensating for the energy exchange between the reactor and the regenerator.

According to one particular embodiment of the invention, the process is performed in a reactor of plate exchanger type. This reactor is constituted of plates, forming between each other circulation channels that may contain a catalyst. This technology has many advantages in terms of heat exchange, associated with a high heat exchange capacity. Thus, this type of reactor is particularly suitable for removing heat easily in the case of exothermic reactions, or for supplying heat in reaction startup phases or in the case of endothermic reactions. More particularly, this reactor makes it possible not only to heat, but also to cool the catalyst. The heat exchange is particularly efficient with the circulation of a heat-exchange fluid in the system. The plates may be assembled in modules and may be stacked. Thus, it is possible to install into the same reaction volume a first stage for the dehydration reaction of glycerol to acrolein, followed by a second stage for the oxidation of acrolein. The modules may be fed with an ascending stream or a descending stream, the stacking of the catalysts being chosen such that the catalyst that becomes deactivated faster is placed on top of the other to facilitate its replacement. Furthermore, the modules may be independently temperature-regulated for better optimization of the reaction. This type of reactor thus involves great flexibility, whether as regards the size of the reactor, its maintenance, or the replacement of the catalyst. Systems that may be suitable for the process of the invention are, for example, the reactors described in documents EP 995 491 or EP 1 147 807, the content of which is incorporated herein by reference. These reactors are particularly suitable for the catalytic inversion of reaction media, specifically gaseous reaction media, such as those used in the present invention. The plate exchanger used for the preparation of (meth)acrolein or (meth)acrylic acid via catalytic oxidation of C3 or C4 precursors, described in document US 2005/0 020 851, may also be suitable for the manufacture of acrylic acid from glycerol, which is the subject of the present invention.

The separation/purification steps must be adapted to the production of acrylic acid, acrylic acid having a higher boiling point than water and acrolein. The acrolein co-produced may be either isolated or recycled to increase the yields of acrylic acid. Moreover, the unselective by-products (other than acrolein and acrylic acid) may be recovered and incinerated, thus producing steam or energy. The energy-upgrading of the by-products of the glycerol oxydehydration reaction furthermore makes it possible to greatly reduce the greenhouse gas emissions of the process, when compared with the conventional process of selective oxidation of propylene, for which the $CO_2$ produced is derived from fossil carbon during the incineration of the by-products.

The experimental conditions of the gas-phase reaction are preferably a temperature of between 250° C. and 350° C. and a pressure of between 1 and 5 bar. To avoid consecutive reactions and the formation of unwanted products, it is important to limit the residence time in the reactor; moreover, by increasing the residence time, it is also possible to have higher conversions. It is especially desirable to increase the contact time (residence time) of the reagents in the region of the catalyst in order to compensate for a decrease in the degree of conversion when a lower reaction temperature is used. When a weakly oxidizing catalyst is used, increasing the temperature allows the acrylic acid yield to be improved.

Glycerol is available in concentrated form, but also in the form of more economical aqueous solutions. Advantageously, an aqueous glycerol solution with a concentration of between 10% and 50% and preferably between 15% and 30% by weight is used in the reactor. The concentration should not be too high, so as to avoid spurious reactions such as the formation of glycerol ethers or reactions between the acrolein or the acrylic acid produced and the glycerol. Moreover, the glycerol solution should not be too dilute on account of the energy cost involved in the evaporation of the aqueous glycerol solution. In any case, the concentration of the glycerol solution may be adjusted by recycling the water produced by the reaction. In order to reduce the glycerol transportation and storage costs, the reactor may be fed with concentrated solution of 40% to 100% by weight, dilution to the optimum content being performed by recycling some of the steam produced by the reaction and of the dilution water. Similarly, the recovery of heat at the reactor outlet may also allow the glycerol solution feeding the reactor to be vaporized.

Glycerol derived from the methanolysis of plant oils in basic medium may contain certain impurities such as sodium chloride or sulfate, non-glycerol organic matter, and methanol. The presence of sodium salts is in particular detrimental to the catalytic dehydration reaction since these salts are capable of poisoning the acidic sites. A pretreatment of the glycerol by ion exchange may be envisioned.

Compared with the conventional process for preparing acrylic acid by selective oxidation of propylene, the acrylic acid produced according to the process of the invention may contain impurities of different nature or in different amount. According to the envisaged use, it may be envisaged to purify the acrylic acid according to the techniques known to those skilled in the art.

The examples that follow illustrate the present invention without, however, limiting its scope.

EXAMPLES

In the examples, a tubular reactor consisting of a tube 85 cm long and with an inside diameter of 6 mm is used to perform the glycerol dehydration reaction in the gas phase at atmospheric pressure. This reactor is placed in a heated chamber maintained at the chosen reaction temperature. The catalysts used are ground and/or pelletized to obtain particles of 0.5 to 1.0 mm. 10 ml of catalyst are loaded into the reactor to form a catalytic bed 35 cm long. This bed is maintained at the reaction temperature for 5 to 10 minutes before introducing the reagents. The reactor is fed with an aqueous solution containing 20% by weight of glycerol at a mean feed flow rate of 12 ml/h, and with a flow rate of 0.8 l/h (13.7 ml/minute) of molecular oxygen for the examples according to the invention, unless otherwise indicated. In this case, the $O_2$/vaporized glycerol/steam relative proportion is 6/4.5/89.5. The aqueous glycerol solution is vaporized in the heated chamber, and then passes over the catalyst. The calculated contact time is about 2.9 sec. After reaction, the products are condensed in a trap refrigerated with crushed ice.

Samples of the effluents are collected periodically. For each sample collection, the stream is interrupted and a gentle stream of nitrogen is passed through the reactor to purge it. The trap at the reactor outlet is then replaced, the nitrogen stream is stopped and the reactor is returned under a stream of reagent.

For each experiment, the total mass of products entering and leaving is measured, which allows a mass balance to be determined. Similarly, the products formed are analyzed by chromatography. Two types of analysis are performed:

an analysis by chromatography on a filled column (FFAP column 2 m*⅛") on a Carlo Erba chromatograph equipped with a TCD detector. The quantitative analysis is performed with an external standard (2-butanone);

an analysis by chromatography on a capillary column (FFAP column 50 m*0.25 mm) on an HP6890 chromatograph equipped with an FID detector with the same samples stored at −15° C.

The first method is particularly suitable for rapid analysis of the products, and especially the yield of acrolein. The second method is used to have a more precise analysis of certain reaction by-products. Moreover, analyses by GC-MS or by chromatography after silylation were performed to confirm these results.

The products thus quantified are the unreacted glycerol, the acrylic acid formed and the acrolein.

In the examples that follow, the glycerol conversion and the yields are defined as follows:

Glycerol conversion (%)=(1−number of moles of glycerol remaining/number of moles of glycerol introduced)×100;

Acrylic acid yield (%)=number of moles of acrylic acid produced/number of moles of glycerol introduced;

Acrolein yield (%)=number of moles of acrolein produced/number of moles of glycerol introduced.

All the results are expressed as molar percentages relative to the glycerol introduced.

Example 1

The following are used as catalyst (10 ml):
(1) a tungsten zirconia (90.7% $ZrO_2$–9.3% $WO_3$) from Daiichi Kigenso (supplier reference H1417), i.e. 17 g,
(2) a sulfate zirconia (90% $ZrO_2$–10% $SO_4$) from Daiichi Kigenso (supplier reference H1416), i.e. 16.5 g,
(3) a phosphate zirconia (91.5% $ZrO_2$–8.5% $PO_4$) from Daiichi Kigenso (reference H1418), i.e. 12.7 g.

The reaction is performed in the absence of oxygen or in the presence of oxygen. The reaction temperature is 300° C. or 350° C. The results are given in the table below.

|  | Catalyst | | | | | | | | |
| --- | --- | --- | --- | --- | --- | --- | --- | --- | --- |
|  | (1) | (1) | (1) | (2) | (2) | (3) | (3) | (3) | (3) |
| Oxygen (ml/minute) | 0 | 13.7 | 13.7 | 0 | 13.7 | 0 | 5.6 | 13.7 | 13.7 |
| Reaction temperature (° C.) | 300 | 300 | 350 | 300 | 300 | 300 | 300 | 300 | 350 |
| Cumulative mass of glycerol introduced (g) | 32 | 32 | 42 | 25 | 25 | 25 | 25 | 42 | 50 |
| Glycerol conversion (%) | 100 | 100 | 100 | 97 | 100 | 100 | 100 | 100 | 100 |
| Acrylic acid yield (%) | 0 | 4.5 | 7.6 | — | 0.9 | 0.3* | 0.7 | 1.1 | 0.7 |
| Acrolein yield (%) | 72.1 | 53 | 19.2 | 40.6 | 52.5 | 46.7 | 43 | 38 | 14.4 |

—: undetermined/
*: uncertain attribution (presence of numerous close peaks)

Example 2

11.8 g of an oxidation catalyst (4) formed by addition of glycerol as binder are used.

Preparation of the Catalyst (4)

The preparation of this type of catalyst is described in patent U.S. Pat. No. 6,310,240.

The precursor is prepared from solutions A and B:

| For solution A | |
|---|---|
| Cold demineralized water | 70 kg |
| Ammonium paratungstate, APT | 3.400 kg |
| Ammonium metavanadate, AMV | 2.810 kg |
| Ammonium heptamolybdate, AHM | 11.590 kg |
| For solution B | |
| Cold demineralized water | 15 kg |
| Strontium nitrate, Sr | 0.590 kg |
| Copper nitrate, Cu | 2.810 kg |

Once a clear solution A has been obtained, precipitation is commenced by introducing solution B into solution A using a cannula, at a flow rate of 30 l/hour: (30 minutes). Solution B is added using a metering pump. The precipitate forms immediately and the solution changes color.

At the end of precipitation (i.e. 2 hours after the start of precipitation), the water is evaporated off and a dry precursor is obtained, which is then precalcined under air at a temperature of 225° C.

A polysilicic acid solution is prepared:
615 g of sodium silicate solution at 28.48 wt % of $Na_2SiO_3$ are added to 2885 g of deionized water to make a solution containing 5% Si. This solution is stirred for 10 minutes at about 1200 rpm. HCR-W2H Dowex ion-exchange resin is added until the pH of the solution is between 2.5 and 3. The slurry is filtered through a Büchner funnel fitted with filter paper, for 10 minutes. The filtrate (3328 g) recovered is orange-brown in color. 1302 g of deionized water are added to the filtrate so as to obtain a solution containing 3.6% of polysilicic acid. About 40 ml of 6.9% sulfuric acid solution are added to the preceding solution so as to lower the pH below 2.5. The solution thus prepared is stored under cold conditions.

The above precalcined solid is micronized so as to obtain a powder of less than 10 microns whose mean particle diameter is from 1 to 1.8 microns.

A slurry containing 34.5 wt % by mass of solid is prepared. The solid contains 60% catalyst, 30% colloidal silica and 10% ex-polysilicic acid silica.

Resin is added to the Nalco colloidal silica solution (50 wt % Nalco 1060), whose starting pH is 8.25, until the pH of the solution is less than 3. Stirring is continued at 400 rpm, and the final pH is 2.0. The slurry is filtered through a Büchner funnel fitted with filter paper. 200 g of the solution thus filtered, 200 g of precalcined solid and 557.3 g of 5% polysilicic acid solution are placed in a flask maintained in ice, and the slurry is stirred at 800 rpm for 15 minutes.

The drying of this slurry is performed in a Bowen atomizer in fountain mode with the following parameters:
inlet air temperature: 370° C.,
air service pressure in the nozzle: about 0.5 bar,
feed rate of the suspension (maintained at 5-10° C. and at a pH of less than 4.0): between 200 and 250 g/minute,
inlet air pressure: 102 mm of water.

During the atomization operation, the exit air temperature falls to 170° C.

The solid obtained is in the form of spherical particles with a density of between 1.0 and 1.1 g/ml and a mean diameter of about 70 microns.

The fraction with a particle size of between 45 and 150 microns is collected by screening. Calcination is performed at 400° C. for 4 hours, in a brick oven, and the powder obtained is sprinkled onto a bed of inert Norton support beads to obtain a ratio of 500 g of powder per 2 kg of Norton support. After calcination, the powder is recovered by screening. The catalyst is formed by adding glycerol as binder.

| Results | | | | |
|---|---|---|---|---|
| Feed of 20% glycerol sol (g/hour) | 7.3 | 8.9 | 8.8 | 6.6 |
| Oxygen (ml/minute) | 20 | 20 | 14 | 20 |
| Reaction temperature (° C.) | 300 | 300 | 300 | 280 |
| Glycerol conversion (%) | 100 | 100 | 95 | 100 |
| Acrylic acid yield (%) | 6.2 | 7.2 | 2.7 | 7.4 |
| Acrolein yield (%) | 2 | 4 | 14 | 3 |

Example 3

The reactor is charged with two successive catalytic beds, the gas stream passing successively through the first bed and then the second.

The first catalytic bed is constituted of 4 ml of catalyst (1) representing a mass of 6.2 g, the second of 10 ml of catalyst (4) formed by adding glycerol as binder, the whole representing a mass of 11.8 g.

In this example, the oxygen is introduced upstream at a rate of 14 ml/minute along with 8 ml/minute of nitrogen.

| Results | | | | |
|---|---|---|---|---|
| Feed of 20% glycerol sol (g/hour) | 6.2 | 4.2 | 4.8 | 6.4 |
| Oxygen/nitrogen (ml/minute) | 14/8 | 14/8 | 14/8 | 14/8 |
| Reaction temperature (° C.) | 260 | 260 | 240 | 220 |
| Glycerol conversion (%) | 100 | 100 | 100 | 100 |
| Acrylic acid yield (%) | 34.6 | 31.3 | 43.6 | 1 |
| Acrolein yield (%) | <0.5 | <0.5 | <0.5 | >1 |

Example 4

The first catalytic bed is constituted of 10 ml of catalyst (1) representing a mass of 12.7 g, the second of 5 ml of catalyst (4) formed by adding acetic acid as binder, the whole representing a mass of 5.25 g. The gas stream passes successively through the first bed and then the second bed.

| Results | | | | | | | |
|---|---|---|---|---|---|---|---|
| Feed of 20% glycerol sol (g/hour) | 9.0 | 8.6 | 9.7 | 9.3 | 9.7 | 9.8 | 9.4 |
| Oxygen (ml/minute) | 14 | 14 | 14 | 14 | 14 | 14 | 14 |
| Reaction temperature (° C.) | 280 | 280 | 280 | 280 | 280 | 280 | 280 |
| Glycerol conversion (%) | 100 | 100 | 100 | 100 | 100 | 100 | 100 |
| Acrylic acid yield (%) | 41.0 | 74.9 | 63.7 | 66.2 | 69.9 | 71.7 | 73.7 |
| Acrolein yield (%) | <0.5 | <0.5 | <0.5 | <0.5 | <0.5 | <0.5 | <0.5 |

Example 5

Example 4 is repeated with variable flow rates of oxygen and nitrogen.

| Results | | | | |
|---|---|---|---|---|
| Feed of 20% glycerol sol (g/hour) | 9 | 9 | 9 | 9 |
| Oxygen/nitrogen (ml/minute) | 8.2/6.4 | 8.2/6.4 | 5.3/9.4 | 6.8/6 |
| Reaction temperature (° C.) | 280 | 260 | 280 | 280 |
| Glycerol conversion (%) | 100 | 100 | 100 | 100 |
| Acrylic acid yield (%) | 71.4 | 37.3 | 57.3 | 70.6 |
| Acrolein yield (%) | <0.5 | 32.5 | 11.7 | <0.5 |

Example 6

The reactor is charged with a first catalytic bed constituted by 10 ml of catalyst (1) representing a mass of 17 g and a second catalytic bed constituted of 5 ml of an oxidation catalyst (5), i.e. a mass of 6 g.

Preparation of Catalyst (5): $MoVo_{0.33}Nb_{0.11}(oxalates)_{0.30}(NH_4)_{1.15}Si_{0.93}O_x$ Preparation of solution A (Mo, V):

The following are introduced into a beaker:
265 g of demineralized water
13.3 g of ammonium metavanadate ($NH_4VO_3$—AMV—from GFE, batch 9811694)
61.0 g of ammonium heptamolybdate ($Mo_7O_{24}(NH_4)_6 \cdot 4H_2O$-AHM-from Starck, batch 064/001).

The mixture is heated to 80° C. with stirring until a clear orange-yellow solution is obtained, i.e. about 30 minutes. The beaker is covered with a watch glass to limit the evaporation.

This solution is then allowed to cool, with stirring, to room temperature.

Preparation of the niobium oxalate solution B:

The following are introduced into a beaker:
80 g of demineralized water
12.9 g of oxalic acid ($C_2H_2O_4 \cdot 2H_2O$ from Prolabo, batch G23G)
6.4 g of niobic acid ($Nb_2O_5 \cdot xH_2O$ from CBMM, 79 wt % after loss on ignition).

The whitish mixture is heated at a temperature of between 60° C. and 70° C. with stirring for two hours. A watch glass is placed on the beaker to limit the evaporation. A clearer solution is obtained, which is centrifuged for 12 minutes at 6200 rpm. After centrifugation, the solution is at room temperature and a light deposit (less than 5 wt %) of undissolved solid remains, which is discarded.

Formation of the Gel 49.2 g of colloidal silica (Ludox 40 wt % of silica) are added to solution A (Mo, V). The niobium oxalate solution B is then added and a thick bright yellow gel is immediately obtained (the stirrer setting needs to be adjusted in order to be able to stir). The mixture is stirred at room temperature for 30 minutes.

Drying of the Gel

The gel obtained is removed and poured into a plate covered with Teflon, and then stoved at 130° C. overnight. About 97.6 g of dry glossy black homogeneous precursor are obtained.

Precalcination

This is performed under a stream of air at 50 ml/min. g for four hours at 300° C. after a temperature gradient of 2° C./minute. 30 g of precursor are used each time, placed in a 120 ml steel vessel. The steel vessel is covered with a lid bearing a hole, and is equipped with a thermometer well to monitor the temperature of the solid during the heat treatment. The temperature is controlled with a thermocouple located in the thermometer well.

Calcination

This is performed under a stream of air at 50 ml/min·g of precursor, for two hours at 600° C. after a temperature gradient of 2° C./minute. The temperature is controlled with a thermocouple located in the thermometer well. The nitrogen is filtered to eliminate any trace of oxygen and moisture, on gas purification cartridges.

| Results | | | | | |
|---|---|---|---|---|---|
| Feed of 20% glycerol sol (g/hour) | 9 | 4.5 | 4.8 | 9 | 9 |
| Oxygen/nitrogen (ml/minute) | 6.5/7 | 6.5/7 | 6.5/7 | 6.5/7 | 6.5/7 |
| Reaction temperature (° C.) | 280 | 280 | 280 | 325 | 350 |
| Glycerol conversion (%) | 100 | 100 | 100 | 100 | 100 |
| Acrylic acid yield (%) | 25.1 | 29.7 | 35 | 31.4 | 7.3 |
| Acrolein yield (%) | 20 | not det. | 4.4 | 24 | not det. |

Example 7

Two separate reactors are used, thus making it possible to adjust the temperature of each reaction and also, if necessary, the composition of the gas streams by means of a side input of gas between the two reactors.

10 ml of catalyst (1) representing a mass of 17 g are placed in the first reactor. 7.5 ml of an oxidation catalyst (6), i.e. a mass of 9.2 g, preceded by 2-3 ml of glass beads, are introduced into the second reactor. The feed rate of the aqueous glycerol solution (20 wt % of glycerol) is set at 21 g/hour.

Oxygen is introduced upstream of the two reactors, the reaction temperatures of which are set at 280° C.

Preparation of Catalyst (6)

This is a catalyst prepared by coating an inert support.

The coater is rotated by means of an electric motor and is heated by a propane flame.

The following starting materials are then prepared:

| | |
|---|---|
| Norton support SA5218 as 5 mm beads | 36 kg |
| For solution A | |
| Cold demineralized water | 70 liters |
| Ammonium paratungstate, APT | 1.700 kg |
| Ammonium metavanadate, AMV | 2.810 kg |
| Ammonium heptamolybdate, AHM | 11.590 kg |
| For solution B | |
| Cold demineralized water | 15 liters |
| Strontium nitrate, Sr | 0.590 kg |
| Copper nitrate, Cu | 2.810 kg |

Solution A is prepared in the coater. Cold water is first introduced, and the coater is then switched on. The coater speed is controlled so as to avoid any overspilling. The tungsten salt (APT), the vanadium salt (AMV) and the molybdenum salt (AHM) are then successively introduced.

The gas (propane) flow rate is then set at 2500 l/hour and heating of the coater is started.

During this time, solution B is prepared. The salts are placed in the provided tank, cold water is poured in, heating of the tank is started and the stirrer is switched on. The flow rate of the solution exiting this tank should be uniform and of 30 l/hour (the tank should be voided in about 30 minutes). A metering pump is used to ensure that there is a constant flow rate during the precipitation phase.

When solution A begins to boil (stable temperature in the region of 100° C.), the propane flow rate is reduced to 2000 l/hour.

10 l of cold demineralized water are added once the solution is at 100° C., while avoiding overspilling of the coater. It takes about one hour to obtain a clear orange-colored solution.

When a clear solution A has been obtained, precipitation is began by pouring solution B into solution A using a cannula, at a flow rate of 30 l/h (in 30 minutes). Solution B is added using a metering pump. The gas (propane) flow rate is then set at 1500 l/hour. The precipitate forms immediately and the solution changes color.

At the end of precipitation (i.e. two hours after the start of the preparation), confirmation is made that there is enough space in the coater, and the entire support is added quickly. The propane flow rate is then reduced to 1000 l/hour. Addition of the support causes a slight cooling of the solution. A few minutes later, the solution is again at the boiling point. The solution is maintained at the boiling point and is allowed to evaporate. This step takes about 1 hour 30 minutes.

At the end of coating, the temperature of the coater is gradually raised, until thoroughly dry beads are obtained. A bead temperature of 108° C. is not exceeded. The coater heating is switched off before this temperature is reached.

The moisture content of the beads is monitored using a Mettler LJ16 infrared desiccator. A sample of about 10 g of beads is taken and placed in the desiccator. The desiccator is programmed to 160° C., duration set to 5 minutes, display in loss of mass mode (wt %). The coating is stopped when the loss of mass steadies between 2.0 wt % and 2.5 wt % (i.e. 30 minutes after stopping the heating).

54 kg of dry precursor are recovered. Fines are occasionally obtained on discharging. In the present case, 0.734 kg of fines is recovered.

The calcination is performed in a brick oven, in aluminum trays equipped with a lid. Six plates of six trays are prepared, six times about 2 kg of precursor are poured into each plate, and the height is equalized. All of the precursor, apart from 1.5 kg collected for sampling, is thus calcined.

The lids are placed on each tray.

The plates are introduced into the oven (which is already at 400° C.), the maximum temperature reached during the calcination is 401° C., and the residence time in the oven is four hours.

After four hours, the plates are removed from the oven while they are still at 400° C. The plates are then left to cool.

48.52 kg, after screening, of gray-black catalyst (6) were thus obtained.

The content of active material bound to the support, determined by chemical stripping, is 27.9 wt %. The tamped packing density is measured on 500 ml of catalyst. The value obtained is 1.37 kg/liter. The mean diameter of the grains is 5.07 mm (mean on 100 grains). The pore volume is measured by mercury porosimetry is 0.1682 ml/g.

| Results | | | | | | |
|---|---|---|---|---|---|---|
| Feed of 20% glycerol sol (g/hour) | 21 | 21 | 21 | 21 | 21 | 21 |
| Oxygen (ml/minute) | 10 | 19 | 32 | 42 | 65 | 88 |
| Reaction temperature (° C.) | 280 | 280 | 280 | 280 | 280 | 280 |
| Glycerol conversion (%) | 100 | 100 | 100 | 100 | 100 | 100 |
| Acrylic acid yield (%) | 45.2 | 63.7 | 68.4 | 69.7 | 68.4 | 65.7 |
| Acrolein yield (%) | 31.1 | 14.2 | 7.7 | 5.4 | 4.0 | 3.9 |

Example 8

Example 7 is repeated, but varying the oxidation temperature, the dehydration reactor temperature being set at 280° C. and the flow rate of oxygen introduced upstream of the two reactors being constant.

| Results | | | | |
|---|---|---|---|---|
| Feed of 20% glycerol sol (g/hour) | 21 | 21 | 21 | 21 |
| Oxygen (ml/minute) | 42 | 42 | 42 | 42 |
| Oxidation reactor temperature (° C.) | 260 | 280 | 300 | 320 |
| Glycerol conversion (%) | 100 | 100 | 100 | 100 |
| Acrylic acid yield (%) | 63.2 | 69.7 | 65.7 | 65.3 |
| Acrolein yield (%) | 9.5 | 5.4 | 3.9 | 1.7 |

Example 9

Example 7 is repeated, but varying the oxygen flow rate in the two reactors. Part of the required oxygen is introduced upstream of the two reactors (oxygen 1), the supplement is supplied via the side entry placed between the two reactors (oxygen 2). The temperature is set at 280° C.

| Results | | | | | | |
|---|---|---|---|---|---|---|
| Oxygen 1 (ml/minute) | 42 | 9 | 20.2 | 20.2 | 88 | 42 |
| Oxygen 2 (ml/minute) | 0 | 32 | 21 | 21 | 0 | 45 |
| Reaction temperature (° C.) | 280 | 280 | 280 | 280 | 280 | 280 |
| Glycerol conversion (%) | 100 | 100 | 100 | 100 | 100 | 100 |
| Acrylic acid yield (%) | 69.7 | 62.2 | 69.3 | 67.3 | 65.7 | 68.4 |
| Acrolein yield (%) | 5.4 | 2.8 | 2.8 | 3.3 | 3.9 | 1.9 |

Example 10

Example 7 is repeated, but the oxygen is replaced with air. The required oxygen, pure or as a mixture, is introduced either in total upstream of the two reactors (gas 1), or a supplement is supplied via the side entry placed between the two reactors (gas 2).

| Results | | | | |
|---|---|---|---|---|
| Gas 1 (ml/minute) | 42-$O_2$ | 88-$O_2$ | 40.8-air | 217-air |
| Gas 2 (ml/minute) | 0 | 0 | 32-$O_2$ | 0 |
| Temperature, ° C. | 280 | 280 | 280 | 280 |
| Glycerol conversion (%) | 100 | 100 | 100 | 100 |
| Acrylic acid yield (%) | 69.7 | 65.7 | 66.1 | 64.1 |
| Acrolein yield (%) | 5.4 | 3.9 | 2.9 | 1.7 |

REFERENCE EXAMPLE

Examples 1 to 5 of patent application WO 05/073 160 are reproduced and named reference examples 1 to 5. The catalysts are prepared according to the described procedure, with the exception of the size of the support material, which is smaller (0.5-1.6 mm), the reaction being performed in reactors of smaller diameter (6 mm instead of 25 mm). Ovens are used as heating systems.

|  | Reference example 1 | Reference example 2 | Reference example 3 | Reference example 4 | Reference example 5 |
| --- | --- | --- | --- | --- | --- |
| Number of reactors | 2 | 2 | 2 | 1 | 1 |
| Temperature, °C. | 1st step: 295 2nd step: 270 | 1st step: 290 2nd step: 270 | 1st step: 292 2nd step: 270 | 295 | 294 |
| % of glycerol in the aqueous sol | 85 | 91 | 92 | 98 | 91 |
| Feed, % glyc./water/$O_2$/$N_2$ | 10/9/6/75 | 14/7/0/79 | 10/4/6/80 | 10/1/6/83 | 10/5/6/79 |
| Duration in hours | 5.5 | 5.5 | 5.7 | 5.5 | 5 |
| Glycerol conversion, % | 100 | 99.5 | 99 | 99.6 | 99.5 |
| Acrylic acid yield, % | 3.89 | 0.39 | 0 | 3.74 | 4.10 |
| Acrolein yield, % | 23.63 | 9.51 | 35.47 | 12.84 | 20.76 |

The results obtained demonstrate the formation of acrolein in larger amount than acrylic acid, which indicates poor activity of the catalyst for the oxidation reaction. Moreover, the acrylic acid and acrolein yields obtained are markedly lower than those indicated in patent application WO 05/073 160.

The invention claimed is:

1. A process for manufacturing acrylic acid from glycerol comprising, feeding glycerol and molecular oxygen to a single reactor wherein the oxydehydration reaction of glycerol in the presence of the molecular oxygen produces acrylic acid.

2. The process as claimed in claim 1, characterized in that the molecular oxygen is in the form of air or in the form of a mixture of gases containing molecular oxygen.

3. The process as claimed in claim 1, characterized in that the glycerol is in the form of an aqueous solution with a concentration of between 10% and 50% by weight in the reactor.

4. The process as claimed in claim 3, characterized in that the glycerol in the reactor is diluted by recycling part of the steam produced by the reaction and dilution water, the reactor being fed with concentrated solutions of from 40% to 100% by weight of glycerol.

5. The process as claimed in claim 1, characterized in that the reaction is performed in the presence of a catalyst selected from: a single catalyst capable of catalyzing both a dehydration reaction and an oxidation reaction, or a mixture of catalysts, a first capable of effecting a dehydration reaction and second capable of effecting an oxidation reaction.

6. The process as claimed in claim 5, characterized in that the single catalyst or the second capable of effecting an oxidation reaction is a solid containing at least one element chosen from Mo, V, W, Re, Cr, Mn, Fe, Co, Ni, Cu, Zn, Sn, Te, Sb, Bi, Pt, Pd, Ru or Rh, present in metallic form, oxide, sulfate or phosphate.

7. The process as claimed in claim 1, characterized in that the reaction is performed in the gas phase.

8. The process as claimed in claim 7, characterized in that the reaction is performed in a fixed-bed reactor, a fluidized-bed reactor or a circulating fluidized-bed reactor.

9. The process as claimed in claim 7, characterized in that the reaction is performed at a temperature of between 250° C. and 350° C.

10. The process as claimed in claim 1, characterized in that the reaction is performed in a plate exchanger.

11. The process as claimed in claim 1, characterized in that the glycerol is in the form of an aqueous solution with a concentration of between 15% and 30% by weight in the reactor.

* * * * *